United States Patent [19]

Kiehs et al.

[11] 4,058,606
[45] Nov. 15, 1977

[54] METHOD OF CONTROLLING INSECTS WITH O,O-DIALKYLPHOSPHONIC ACID ESTERS AND THE O,O-DIALKYLPHOSPHONIC ACID ESTERS

[75] Inventors: Karl Kiehs, Lampertheim; Heinrich Adolphi, Limburgerhof; Rolf Huber, Ludwigshafen; Annegrit Baumann, Mannheim, all of Germany

[73] Assignee: BASF Aktiengesellschaft, Ludwigshafen (Rhine), Germany

[21] Appl. No.: 661,797

[22] Filed: Feb. 26, 1976

[30] Foreign Application Priority Data

Mar. 25, 1975 Germany .............................. 2513126

[51] Int. Cl.$^2$ ............................ A01N 9/36; C07F 9/32

[52] U.S. Cl. ............................ 424/217; 260/345.9 R; 260/347.8; 260/950; 260/951; 424/283

[58] Field of Search ................. 260/950, 951; 424/217

[56] References Cited

U.S. PATENT DOCUMENTS 2,962,518  11/1960  Lorenz et al. ....................... 260/953

*Primary Examiner*—Anton H. Sutto
*Attorney, Agent, or Firm*—Keil, Thompson & Shurtleff

[57] ABSTRACT

New O,O-dialkylphosphonic acid esters having a strong insecticidal action, insecticides containing these compounds as active ingredients, a method of controlling insects, and a method for the preparation of the active ingredients.

10 Claims, No Drawings

METHOD OF CONTROLLING INSECTS WITH O,O-DIALKYLPHOSPHONIC ACID ESTERS AND THE O,O-DIALKYLPHOSPHONIC ACID ESTERS

The present invention relates to new and valuable O,O-dialkyl-phosphonic acid esters having a strong insecticidal action, insecticides containing these compounds as active ingredients, a method of controlling insects, and a method for the preparation of the active ingredients.

It is known (German 977,119) to use O,O-dimethyl-(2,2,2-trichloro-1hydroxyethyl)-phosphonate as an insecticide. However, its action is poor.

We have now found that O,O-dialkylphosphonic acid ester derivatives of the formula $$\begin{array}{c} R^1O \\ \diagdown \\ P \\ \diagup \\ R^1O \end{array} \begin{array}{c} O \\ \diagup\!\!\!\diagup \\ \diagdown \\ CH-CCl_3 \\ | \\ O-CH-R^2 \\ | \\ O-R^3 \end{array} \qquad I,$$

where $R^1$ denotes alkyl of from 1 to 3 carbon atoms, $R^2$ denotes alkyl of from 1 to 3 carbon atoms, $R^3$ denotes alkyl of from 1 to 4 carbon atoms, phenyl, or haloalkyl of a maximum of 4 carbon atoms, and $R^2$ and $R^3$, together with the atoms whose substituents they are, denote a 5-or 6-membered oxygen-containing heterocyclic ring, have a better insecticidal action than prior art compounds.

Suitable substituents for $R^1$ and $R^2$ are methyl, ethyl and propyl, especially methyl, ethyl and isopropyl. $R^3$ is preferably methyl, ethyl, isopropyl, isobutyl, phenyl and haloalkyl, especially chloroethyl and bromoethyl. Suitable 5- or 6-membered heterocyclic rings are tetrahydrofuran, tetrahydropyran, and methyl-substituted pyran rings, for instance 2- and 3-methyltetrahydropyran.

The new active ingredients may be prepared by reacting prior art O,O-dialkylphosphonic acid esters of the formula $$\begin{array}{c} R^1O \\ \diagdown \\ P \\ \diagup \\ R^1O \end{array} \begin{array}{c} O \\ \diagup\!\!\!\diagup \\ \diagdown \\ CH-CCL_3, \\ | \\ OH \end{array}$$

where $R^1$ has the above meanings, with vinyl ethers of the formula $$\begin{array}{c} R^4 \\ \diagdown \\ C=CH-O-R^3, \\ \diagup \\ R^5 \end{array}$$

where $R^3$ has the above meanings and $R^4$ and $R^5$ are identical or different and denote hydrogen or methyl.

The starting materials are synthesized in known manner.

The new active ingredients are expediently prepared in an inert solvent; suitable solvents are all those which dissolve the reactants to a sufficient extent, e.g., aromatic hydrocarbons (benzene, toluene, xylene), chlorinated or nitrated aromatic hydrocarbons and chlorinated or nitrated aliphatic hydrocarbons (e.g., $CH_2Cl_2$, $CHCl_3$, $CCl_4$, $CH_2Cl-CH_2Cl$, $CH_2Cl-CHCl_2$, $CH_3NO_2$, $C_2H_5NO_2$, etc.), aliphatic nitriles, cyclic or acyclic ethers (anisole, dioxane, diisopropyl ether, tetrahydrofuran), and aliphatic, cyclic and acyclic ketones (acetone, methyl ethyl ketone, cyclohexanone).

It is advantageous to prepare the new phosphonic acid esters in the presence of catalytic amounts of an acid. Examples of suitable acids are HCl, HBr, HI, $H_2SO_4$, $H_3PO_4$, $HClO_4$, $CCl_3COOH$, ⌬—$SO_3H$, $SOCl_2$, $BF_3O(C_2H_5)_2$, and $ZnCl_2$.

The reaction temperatures may be varied within a wide range, the upper limit to which is set by the decomposition temperature of the starting materials. The preferred temperature range is from 0° to 60° C. The new phosphonic acid esters are oils of a yellowish to dark color.

The compounds have an excellent action on insects, especially caterpillars and Diptera, and are eminently suited for combatting such pests and other Articulata.

Examples of such pests are as follows:
*Ceratitis capitata*
*Dacus dorsalis*
*Lucilia cuprina*
*Musca domestica*
*Fannia canicularis*
*Psila rosae*
*Hylemya antiqua*
*Hylemya brassicae*
*Plutella maculipennis*
*Barathra brassicae*
*Heliothis zea*
*Heliothis virescens*
*Spodoptera littoralis*
*Laphygma exigua*
*Laphygma frugiperda*
*Chilo zonellus*
*Chilo suppressalis*
*Capua reticulana*
*Cydia pomonella*
*Earias insulana*
*Pectinophora gossypiella*
*Diabrotica spec.*
*Epilachna varivestris*
*Leptinotarsa decemlineata*
*Athalia colibri*
*Aphis fabae* etc.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc, are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates,, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients oils of various types, herbicides, fungicides, nematocides, insecticides, bactericides, trace elements, fertilizers, antifoams (e.g., silicones), and growth regulators.

The following examples illustrate the preparation and use of the new compounds.

EXAMPLE 1

O,O-dimethyl-[1-(1-methoxy)-ethoxy-2,2,2-trichloroethyl]-phosphonate

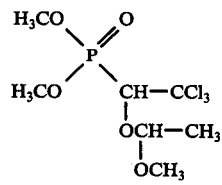

0.2 mole of O,O-dimethyl-(1-hydroxy-2,2,2-trichloroethyl)-phosphonate is mixed in toluene with one drop of thionyl chloride.

At 0° C, 0.22 mole of methyl vinyl ether is added. The mixture is heated to room temperature, whereupon the temperature then rises considerably. It is kept at 60° C by cooling. The mixture is stirred for 30 minutes at 50° C and then worked up by washing the toluene phase first with triethylamine solution and then with $H_2O$, $NaHCO_3$ and again with $H_2O$. The organic phase is dried and evaporated. After removal of the solvent, the substance is freed from readily volatile impurities under an oil pump vacuum for 1 hour at 60° to 70° C.

Yield: 51 g of a pale yellow oil;
$n_D^{25}$: 1.4815

|        | C    | H   | O    | Cl   | P   |
|--------|------|-----|------|------|-----|
| calc.: | 26.6 | 4.5 | 25.4 | 33.7 | 9.8 |
| found: | 26.5 | 4.5 | 25.0 | 33.5 | 9.8 |

EXAMPLE 2

O,O-diethyl-[1-(2-chloroethoxy)-2,2,2-trichloroethyl]-phosphonate

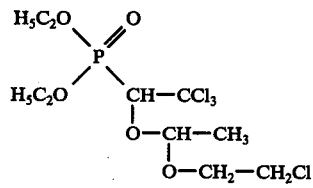

0.1 mole of O,O-diethyl-(1-hydroxy-2,2,2-trichloroethyl)-phosphonate is mixed with 1 drop of thionyl chloride and 100 ml of absolute acetonitrile.

At 35° C, 0.11 mole of β-chloroethyl vinyl ether is dripped in and the mixture refluxed for 90 minutes. Working up and further treatment are as in Example 1.

Yield: 26 g of a dark oil;
$n_D^{25}$: 1.4748

|        | C    | H   | O    | Cl   | P   |
|--------|------|-----|------|------|-----|
| calc.: | 30.6 | 4.9 | 20.4 | 36.2 | 7.9 |
| found: | 30.9 | 4.8 | 20.5 | 35.6 | 8.0 |

EXAMPLE 3

O,O-dimethyl-[1-(1-ethoxy)-propyloxy-2,2,2-trichloro-ethyl]-phosphonate

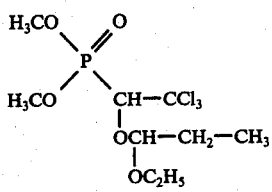

0.1 mole of O,O-dimethyl-(1-hydroxy-2,2,2-trichloro-ethyl)-phosphonate is mixed with 1 drop of thionyl chloride and 100 ml of absolute toluene.

At 40° C, 0.11 mole of ethylpropenyl-(1)-ether is dripped in. After 1 hour at 40° C and 1 hour at 50° C the mixture is worked up as described in Example 1.

Yield: 8 g;
b.p. (0.04 mm): 70° to 75° C

|        | C    | H   | Cl   | P   |
|--------|------|-----|------|-----|
| calc.: | 31.5 | 5.3 | 31.0 | 9.0 |
| found: | 32.2 | 5.1 | 31.4 | 9.1 |

The following compounds were prepared analogously:

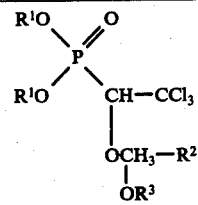

| $R^1$ | $R^2$ | $R^3$ | $n_D^{25}$ |
|---|---|---|---|
| $CH_3$ | $CH_3$ | $CH_2CH_2Cl$ | 1.4851 |
| $CH_3$ | $CH_3$ | $C_2H_5$ | 1.4752 |
| $CH_3$ | $CH_3$ | $-CH_2-CH(CH_3)_2$ | 1.4719 |
| $CH_3$ | $i\text{-}C_3H_7$ | $C_2H_5$ | 1.4561 |
| $CH_3$ | $CH_3$ | $i\text{-}C_3H_7$ | 1.4718 |
| $C_2H_5$ | $CH_3$ | $CH_3$ | 1.4681 |
| $C_2H_5$ | $CH_3$ | $C_2H_5$ | 1.4652 |
| $C_2H_5$ | $CH_3$ | $-CH_2-CH(CH_3)_2$ | 1.4622 |
| $C_2H_5$ | $CH_3$ | $i\text{-}C_3H_7$ | 1.4580 |
| $i\text{-}C_3H_7$ | $CH_3$ | $CH_3$ | |
| $i\text{-}C_3H_7$ | $CH_3$ | $C_2H_5$ | |
| $i\text{-}C_3H_7$ | $i\text{-}C_3H_7$ | $C_2H_5$ | |
| $i\text{-}C_3H_7$ | $CH_3$ | $i\text{-}C_3H_7$ | |
| $CH_3$ | $CH_3$ | 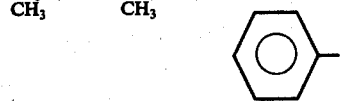 | 1.5147 |
| $CH_3$ |  | | |
| $CH_3$ |  | | 1.4931 |
| $C_2H_5$ |  | | 1.4789 |
| $CH_3$ | 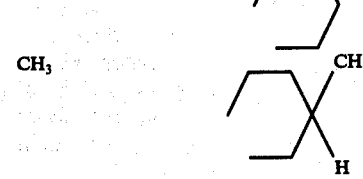 | | 1.4890 |

-continued

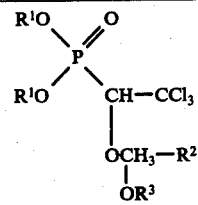

| $R^1$ | $R^2$ | $R^3$ | $n_D^{25}$ |
|---|---|---|---|
| $C_2H_5$ | | (branched alkyl with CH₃'s and H) | 1.4732 |

The insecticidal action is demonstrated in the following examples.

The active ingredients according to the invention which were used are as follows:

1.
$$\begin{array}{c} CH_3-O \\ CH_3-O \end{array}\!\!\!P(=O)-CH-CCl_3 \atop \phantom{XXX} O-CH-CH_3 \atop \phantom{XXXXX} O-CH_3$$

2.
$$\begin{array}{c} CH_3-O \\ CH_3-O \end{array}\!\!\!P(=O)-CH-CCl_3 \atop \phantom{XXX} O-CH-CH_2-CH_3 \atop \phantom{XXXXX} O-C_2H_5$$

3.
$$\begin{array}{c} CH_3-O \\ CH_3-O \end{array}\!\!\!P(=O)-CH-CCl_3 \atop \phantom{XXX} O-CH-CH_3 \atop \phantom{XXXXX} O-CH_2-CH_2Cl$$

4.
$$\begin{array}{c} CH_3-O \\ CH_3-O \end{array}\!\!\!P(=O)-CH-CCl_3 \atop \phantom{XXX} O-CH-CH_3 \atop \phantom{XXXXX} O-C_2H_5$$

5.
$$\begin{array}{c} CH_3-O \\ CH_3-O \end{array}\!\!\!P(=O)-CH-CCl_3 \atop \phantom{XXX} O-CH-CH_3 \phantom{XX} CH_3 \atop \phantom{XXXXX} O-CH_2-CH \atop \phantom{XXXXXXXX} CH_3$$

6.
$$\begin{array}{c} CH_3-O \\ CH_3-O \end{array}\!\!\!P(=O)-CH-CCl_3 \atop \phantom{XXX} O-CH-CH_3 \atop \phantom{XXXXX} O-C_6H_5$$

7.
$$\begin{array}{c} CH_3-O \\ CH_3-O \end{array}\!\!\!P(=O)-CH-CCl_3 \phantom{XX} CH_3 \atop \phantom{XXX} O-CH-CH- \atop \phantom{XXXXXXXX} CH_3 \atop \phantom{XXXXX} O-C_2H_5$$

-continued

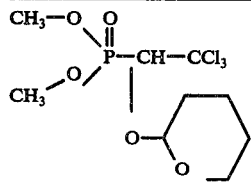
8.

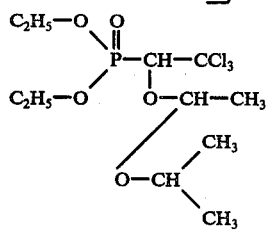
9.

Prior art agent used for comparison purposes was

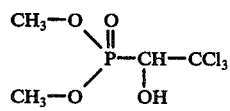
I

EXAMPLE 4

Action on caterpillars of the cabbage moth *(Plutella maculipennis)*

Young cabbage leaves are dipped for 3 seconds into aqueous formulations of the active ingredients. After the coating has dried, the leaves are placed on glass dishes. Ten caterpillars (third to fourth stage) are then put in each dish.

The kill rate is determined after 48 hours.

Results:

| Active ingredient | Amount of active ingredient in aqueous formulation in wt% | Mortality |
|---|---|---|
| 1 | 0.01 | 100% |
| 2 | 0.01 | 100% |
|   | 0.005 | 90% |
| 4 | 0.01 | 100% |
|   | 0.005 | 90% |
| 5 | 0.01 | 100% |
|   | 0.005 | 90% |
| 6 | 0.01 | 100% |
|   | 0.005 | 80% |
| 7 | 0.01 | 100% |
|   | 0.005 | 90% |
| 8 | 0.01 | 100% |
|   | 0.005 | 80% |
| 9 | 0.02 | 100% |
|   | 0.01 | 90% |
| I | 0.02 | 100% |
|   | 0.01 | 40% |

EXAMPLE 5

Continuous contact action on houseflies *(Musca domestica)*

Glass dishes 10 cm in diameter are wetted with acetonic active ingredient solutions of different concentrations. After evaporation of the solvent, 10 houseflies (4 days old) are placed on the dishes.

The kill rate is determined after 4 hours.

Results:

| Active ingredient | Amount of active ingredient per dish in mg | Mortality |
|---|---|---|
| 1 | 0.005 | 100% |
| 3 | 0.005 | 90% |
| 8 | 0.0025 | 100% |
| I | 0.01 | 100% |
|   | 0.005 | 70% |

EXAMPLE 6

Administration test on houseflies *(Musca domestica)*

Acetonic solutions of the active ingredients are dipped on to the ventral abdomen of 4-day-old houseflies under mild $CO_2$ narcosis.

The action, from which the $LD_{50}$ is calculated, is determined after 4 hours.

Results:

| Active ingredient | $LD_{50}$ per fly in $\mu g$ |
|---|---|
| 1 | 0.1 |
| 5 | 0.4 |
| 6 | 0.2 |
| 8 | 0.17 |
| I | 1.3 |

EXAMPLE 7

Action on bean aphids *(Aphis fabae)*

Bean plants *(Vicia faba)* heavily infected by bean aphids are sprayed to run-off with aqueous active ingredient formulations of various concentrations.

The kill rate is determined after 24 hours.

Results:

| Active ingredient | Amount of active ingredient in solution in wt% | Mortality |
|---|---|---|
| 1 | 0.025 | 100% |
| 2 | 0.025 | 100% |
| 6 | 0.04 | 100% |
| 7 | 0.05 | 100% |
| 8 | 0.04 | 100% |
| I | 0.1 | 95% |
|   | 0.05 | 80% |

The comparative experiments demonstrate the superior insecticidal action of the new compounds over the prior art compound.

EXAMPLE 8

90 parts by weight of 0,0-dimethyl-[1-(methoxy)-ethoxy-2,2,2-trichloroethyl]-phosphonate is mixed with 10 parts by weight of N-methyl-α-pyrrolidone. A mixture is obtained which is suitable for application in the form of very fine drops.

EXAMPLE 9

20 parts by weight of 0,0-diethyl-[1-(2-chloroethoxy)-ethoxy-2,2,2-trichloroethyl]-phosphonate is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of 0,0-dimethyl-(1-tetrahydropyranyl-(2)-oxy-2,2,2-trichloroethyl)-phosphonate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of 0,0-diethyl-[1-(2-chloroethoxy)-ethoxy-2,2,2-trichloroethyl]-phosphonate is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 12

20 parts by weight of 0,0-dimethyl-[1-(1-ethoxy-)-n-propyloxy-2,2,2-trichloroethyl]-phosphonate is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by eight of powdered silica gel, and triturated in a hammer mill. By uniformly distributing the mixture in 20,000 parts by weight of water, a spray liquid is obtained containing 0.1% by weight of the active ingredient.

EXAMPLE 13

3 parts by weight of 0,0-dimethyl-[1-(1-ethoxy)-ethoxy-2,2,2-trichloroethyl]-phosphonate is intimately mixed with 97 parts by weight of particulate kaolin. A dust is obtained containing 3% by weight of the active ingredient.

EXAMPLE 14

30 parts by weight of 0,0-dimethyl-[1-(1-phenoxy)-ethoxy-2,2,2-trichloroethyl]-phosphonate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A method of combatting insects wherein the insects are treated with a phosphonic acid ester derivative of the formula

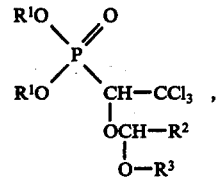

wherein $R^1$ denotes alkyl of from 1 to 3 carbon atoms, $R^2$ denotes alkyl of from 1 to 3 carbon atoms, $R^3$ denotes alkyl of from 1 to 4 carbon atoms, phenyl, or haloalkyl of a maximum of 4 carbon atoms.

2. A method as claimed in claim 1 wherein $R^3$ denotes alkyl of 1 to 4 carbon atoms, phenyl or haloalkyl of a maximum of 4 carbon atoms.

3. A method as claimed in claim 1 wherein $R^3$ denotes alkyl of 1 to 4 carbon atoms or haloalkyl of a maximum of 4 carbon atoms.

4. A method as claimed in claim 1 wherein $R^3$ denotes methyl, ethyl, isopropyl, isobutyl, chloroethyl or bromoethyl.

5. A phosphonic acid ester derivative of the formula

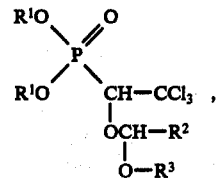

where $R^1$ denotes alkyl of from 1 to 3 carbon atoms, $R^2$ denotes alkyl of from 1 to 3 carbon atoms, $R^3$ denotes alkyl of from 1 to 4 carbon atoms, phenyl, or haloalkyl of a maximum of 4 carbon atoms.

6. A phosphonic acid ester derivatives as claimed in claim 5 wherein $R^3$ denotes alkyl of 1 to 4 carbon atoms, phenyl or haloalkyl of a maximum of 4 carbon atoms.

7. A phosphonic acid ester derivative as claimed in claim 5 wherein $R^3$ denotes alkyl of 1 to 4 carbon atoms or haloalkyl of a maximum of 4 carbon atoms.

8. A phosphonic acid ester derivative as claimed in claim 5 wherein $R^3$ denotes chloroethyl or bromoethyl.

9. A phosphonic acid ester derivative as claimed in claim 5 wherein $R^3$ denotes methyl, ethyl, isopropyl or isobutyl and $R^1$ and $R^2$ denote methyl, ethyl or isopropyl.

10. An insecticide containing as active component a phosphonic acid ester derivative as claimed in claim 5.